US00PP28386P3

(12) United States Plant Patent
Fell

(10) Patent No.: US PP28,386 P3
(45) Date of Patent: Sep. 12, 2017

(54) ***NEOREGELIA* PLANT NAMED 'VD001'**

(50) Latin Name: ***Neoregelia* hybrid**
Varietal Denomination: VD001

(71) Applicant: David Fell, Waimanalo, HI (US)

(72) Inventor: David Fell, Waimanalo, HI (US)

( * ) Notice: Subject to any disclaimer, the term of this patent is extended or adjusted under 35 U.S.C. 154(b) by 139 days.

(21) Appl. No.: 14/756,036

(22) Filed: Jul. 22, 2015

(65) Prior Publication Data

US 2017/0027094 P1 Jan. 26, 2017

(51) Int. Cl.
*A01H 5/12* (2006.01)

(52) U.S. Cl.
USPC ..... Plt./370

(58) Field of Classification Search
USPC ..... Plt./263.1, 373, 370
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Neoregelia* cultivar named 'VD001' is disclosed, characterized by very bright pink foliage margins and significant contrasting foliage color which is maintained under a variety of conditions. The new variety is a *Neoregelia*, suitable for ornamental plant purposes.

1 Drawing Sheet

Latin name of the genus and species: *Neoregelia* hybrid. Variety denomination: 'VD001'.

BACKGROUND OF THE INVENTION

The new cultivar is a product of a chance discovery. The new variety originated as a whole plant mutation occurring among tissue culture plants of *Neoregelia* 'Voodoo Doll'. The initial identification of the sport was made in Florida, with the tissue culture mutant then sent to Hawaii. The inventor then observed and propagated the clone to assess stability. Selection of 'VD001' was made during 2014.

Asexual reproduction of the new cultivar 'VD001' was first performed by vegetative cuttings in 2014 in Waimanalo, Hi. 'VD001' has been reproduced over 6 generations and has shown that the unique features of this cultivar are stable and reproduced true to type.

SUMMARY OF THE INVENTION

The cultivar 'VD001' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'VD001' These characteristics in combination distinguish 'VD001' as a new and distinct *Neoregelia* cultivar:

1. Bright pink margins.
2. Margin coloration is maintained in different light levels.
3. Margin coloration is maintained under different fertilizer regimes.
4. Unique and significant contrasting coloration of foliage.

COMPARISON TO PARENT VARIETY

Plants of the new cultivar 'VD001' are similar to the parent variety in most horticultural characteristics, however, the new variety differs in the following:

1. Marginated coloration, the parent variety has solid leaf coloration.
2. Ease of bright coloration development: the parent variety does not easily develop an attractive bright color.
3. Bright color begins earlier in the new variety, when produced from cuttings.
4. The new variety has a more significant contrasting coloration of foliage.

COMMERCIAL COMPARISON

'VD001' can also be compared to it *Neoregelia* 'Luna Marginated', unpatented. The varieties are similar in some horticultural characteristics, however, the new variety differs in the following:

1. Leaves of the new variety are bronze/green/purple, whereas foliage of the comparator is green with pink.
2. The new variety has a much more intense pink margination.
3. Overall coloration of the new variety is deeper.

'VD001' can also be compared to it *Neoregelia* 'Raphael', U.S. Plant Pat. No. 10,719. The varieties are similar in some horticultural characteristics, however, the new variety differs in the following:

1. Leaves of the 'Rafael' change to green and white under low light conditions, the new variety maintains its coloration better in low light.
2. The new variety has a much more intense pink margination.
3. Center leaf color of the new variety is significantly darker.
4. Older foliage of the comparator turns green, the new variety maintains its contrasting coloration with age.

BRIEF DESCRIPTION OF THE PHOTOGRAPH

The accompanying photograph in FIG. 1 illustrates in full color a typical plant of 'VD001' grown in a greenhouse. This plant is approximately 1 year old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'VD001' plants grown in a climate controlled greenhouse in Hawaii. Temperatures ranged from approximately 18° C. to 22° C. at night to 18° C. to 22° C. during the day. No artificial light, photoperiodic treatments or chemical treatments were given to the plants. Measurements and numerical values represent averages of typical plant types.

Botanical classification: *Neoregelia* hybrid 'VD001'

PROPAGATION

Time to rooting: 2 months from a 2 year old tissue culture at approximately 20 to 22° C.

Root description: Fine, fibrous. Free Branching.

PLANT

Growth habit: Flat rosettes around a single axis.
Plant shape: Flattened sphere.
Height: Approximately 18.0 cm.
Plant spread: Approximately 58 cm.
Normal pot size: 6 inch and larger.
Growth rate: Moderate.
Branching characteristics: Upright, non-branching.
Number of leaves per plant: Approximately 30.
Age of plant described: Approximately 1 year.

FOLIAGE

Leaf:

*Arrangement*.—Whorled.
*Average length*.—Average range 20 to 28 cm.
*Average width*.—Average range 6.0 to 7.5 cm.
*Shape of blade*.—Oblong.
*Aspect*.—Slightly recurved.
*Angle of attachment*.—Approximately 0° to 15° degrees from center of plant. Nearly flat.
*Apex*.—Short apiculate.
*Base*.—Decurrent.
*Margin*.—Evenly and sharply serrate.
*Texture of top surface*.—Smooth, moderately glossy.
*Texture of bottom surface*.—Smooth, glossy.
*Color*.—Young foliage upper side: Main color between Red-Purple 72B and N74A. Thin stripes near Greyed-Green N189A, thicker stripes near Red-Purple 72C. Margin near Red-Purple N74A. Young foliage under side: Near R.H.S. Red-Purple 72B, thick stripes near Greyed-Purple N186B. Thinner stripes near Greyed-Purple 186A, 186B and 186C, colors present separately. Margin near Red-Purple N74A. Mature foliage upper side: Main color near Greyed-Purple N186D. Thin mid stripes and margins near Red-Purple N74A. Mature foliage under side: Main color near Greyed-Purple N186D. Thin mid stripes and margins near Red-Purple N74A.

Venation:

*Type*.—Parallel.
*Venation coloration*.—Identical/Indistinguishable from foliage.

Petiole: Not present, sessile.

FLOWER

Flowering has not been observed, and is not commercially important in this cultivar.

OTHER CHARACTERISTICS

Disease resistance: Neither resistance nor susceptibility to diseases or pests has been observed in this variety.

Drought tolerance and cold tolerance: Observed to tolerate temperatures to 35° C. without any negative effects. Temperature tolerance above this range has not been observed. Tolerance of cold temperatures have not been observed.

Fruit/seed production: Not observed.

What is claimed is:

1. A new and distinct cultivar of *Neoregelia* plant named 'VD001' as herein illustrated and described.

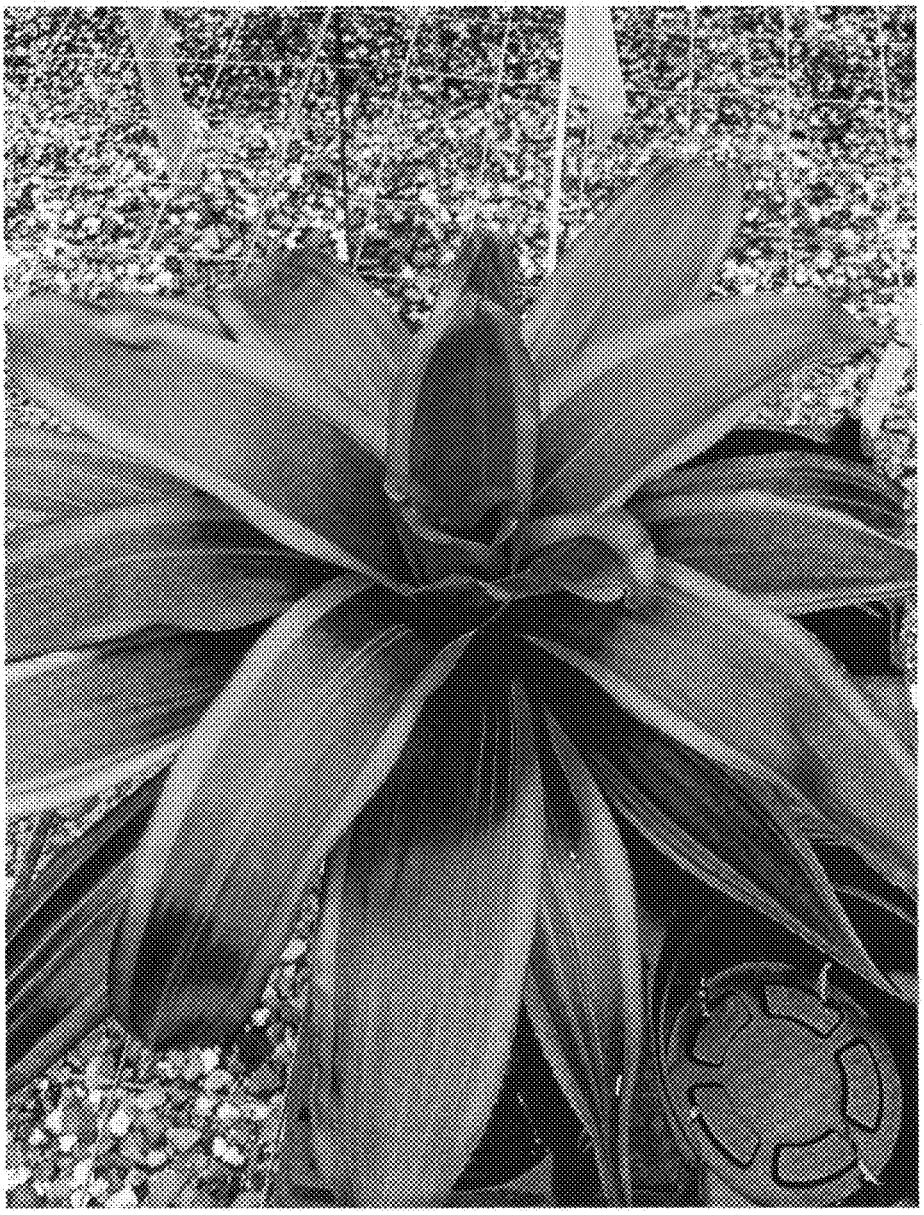

* * * * *